United States Patent [19]
Satzinger et al.

[11] 3,957,851
[45] *May 18, 1976

[54] 1-PHENYL-4-AMINO-CYCLOHEX-2-ENE-1-CARBOXYLIC ACID ETHYL ESTERS

[75] Inventors: Gerhard Satzinger; Manfred Franz Herrmann, both of Gundelfingen, Germany

[73] Assignee: Warner-Lambert Company, Morris Plains, N.J.

[ * ] Notice: The portion of the term of this patent subsequent to Sept. 16, 1992, has been disclaimed.

[22] Filed: Feb. 15, 1972

[21] Appl. No.: 226,509

[30] Foreign Application Priority Data
Feb. 18, 1971 Germany............................ 2107871

[52] U.S. Cl. ..................... 260/471 A; 260/247.2 B; 260/268 R; 260/268 C; 260/268 PH; 260/293.81; 260/293.82; 260/456 R; 260/456 P; 260/469; 260/471 R; 260/473 R; 424/248; 424/250; 424/267; 424/309
[51] Int. Cl.$^2$........................................ C07C 101/38
[58] Field of Search.................... 260/471 A, 293.81

[56] References Cited
UNITED STATES PATENTS
3,557,127  1/1971  Satzinger ....................... 260/293.81

OTHER PUBLICATIONS
C.A. 74: 91,163x (1971) Satzinger et al.

Primary Examiner—Sherman D. Winters
Attorney, Agent, or Firm—Albert H. Graddis; Frank S. Chow; George M. Yahwak

[57] ABSTRACT

The invention relates to 1-phenyl-4-amino-cyclohex-2-ene-1-carboxylic-acid-esters of the general formula I

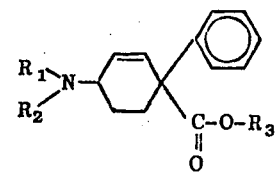

wherein $R_1$ and $R_2$ may be the same or different and may be H, alkyl, hydroxyalkyl, alkenyl, preferably with 1 to 4 C-atoms, aralkyl which may be bonded to each other, in which connection the heterocyclic system formed may be substituted further by the OH— group and where attachment takes place by an oxygen or a nitrogen atom, if desired, which in its turn carries an H, alkyl with 1 to 4 C-atoms, aryl which may be substituted by chlorine, preferably in 3 or 4-position, and by methoxy, preferably in 2 or 4-position, acyl, preferably alkanoyl with 1 to 4 C-atoms, and aroyl, or aralkyl, and $R_3$ represents an alkyl radical with 1 to 4 C-atoms, the salts thereof and quarternary ammonium compounds, and a process for their preparation. These compounds have analgesic and neuroleptic properties.

9 Claims, No Drawings

1-PHENYL-4-AMINO-CYCLOHEX-2-ENE-1-CARBOXYLIC ACID ETHYL ESTERS

It has been surprisingly found that cyclohexenes of the general formula II:

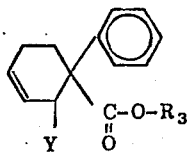

wherein Y means a nucleophilically exchangeable group such as Cl—, Br—, J—, $CH_3SO_2$—O—, p—$CH_3$—$C_6H_4$—$SO_2$—O—, $C_6H_5SO_2$—O—, p—Br— —$C_6H_4SO_2$—O—, p—$NO_2$—$C_6H_4$—$SO_2$—O—, p—$NO_2$—$C_6H_4$—CO—O— etc. react with amines of the general formula H—$NR_1$—$R_2$ in a smooth reaction to form 1-phenyl-4-amino-cyclohex-2-ene-1-carboxylic-acid-esters of the general formula I

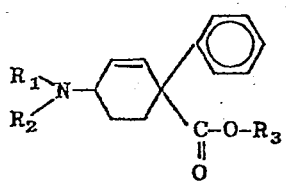

wherein $R_1$ and $R_2$ may be the same or different and may be H, alkyl, hydroxyalkyl, alkenyl, preferably with 1 to 4 C-atoms, aralkyl which may be bonded to each other, in which connection the heterocyclic system formed may be substituted further by the OH- group and where attachment takes place by an oxygen or a nitrogen atom, if desired, which in its turn carries an H, alkyl with 1 to 4 C-atoms, aryl which may be substituted by chlorine, preferably in 3 or 4-position, and by methoxy, preferably in 2 or 4-position, acyl, preferably alkanoyl with 1 to 4 C-atoms, and aroyl, or aralkyl, and $R_3$ represents an alkyl radical with 1 to 4 C-atoms.

In general the reaction is performed by allowing the amines $HNR_1R_2$ to react with the compounds II in an organic solvent, preferably in dioxane, dimethylformamide, dimethylsulfoxide, ethanol or acetonitrile, occasionally, however, also in the absence of a solvent in the presence or in the absence of an auxiliary base, at temperatures between 10° and 160°C.

According to the invention it is possible, furthermore, to transform a compound of the general formula I into the acid addition salt according to previously known methods, e.g. by treatment with a physiologically acceptable inorganic or organic acid such as hydrochloric acid, phosphoric acid, sulphuric acid or tartaric acid, fumaric acid, ascorbic acid, oxalic acid etc. It is possible, too, to quaternize a compound of the general formula I at the nitrogen, according to the usual methods, e.g. by treatment with an alkyl halide.

According to the invention the compounds of the general formula II can be prepared by various methods.

a. A cyclohexene derivative of the general formula III

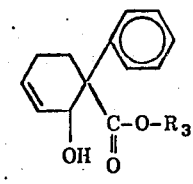

($R_3$ has the above meaning) can be reacted with acid halides, such as $PCl_5$, $POCl_3$, $PBr_3$, $POBr_3$, $SOCl_2$, $CH_3COBr$ etc. or with hydro halogenic acids, in a fundamentally known manner. Preferably this reaction is performed in an inert solvent, such as benzene, chloroform or carbon tetrachloride; reaction with hydro halogenic acids, however, may also be successfully effected in the aqueous or alcoholic phase or in glacial acetic acid.

b. A cyclohexene derivative of the general formula III can be reacted with a sulphonic acid chloride, such as methanesulphonic acid chloride, p-toluenesulphonic acid chloride, p-nitrobenzenesulphonic acid chloride etc., in a fundamentally known manner in the presence of a base, preferably in the presence of pyridine, using a solvent or not.

c. The 1-phenyl-2-acetoxy-cyclohex-3-ene-1-carboxylic-acid-esters of the general formula IV, preparation of which according to the invention is described below, can be converted directly into compounds of the general formula II (for Y = halogen) by treatment with aqueous-hydro halogenic acids or with thionyl halides.

d. The 1-phenyl-2-dialkylamino-cyclohex-3-ene-1-carboxylic-acid esters can be converted directly into the compounds of the general formula II (for Y = J) by reaction with at least 2 equivalents of alkyliodide in an inert solvent, at temperatures between 15° and 80°C; this reaction will be illustrated by the following example:

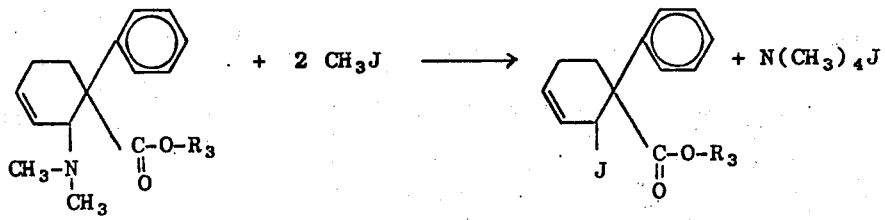

The 1-phenyl-2-acetoxy-cyclohex-3-ene-1-carboxylic-acid-esters of the general formula IV

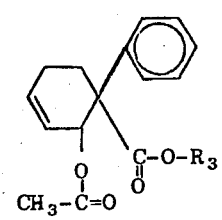

used as the starting material, are prepared according to the invention by a one-container-reaction of the components crotonaldehyde, acetanhydride and ethyl atropate, in the presence of anhydrous sodium acetate. In detail, the process is as follows: The ethyl atropate and the crotonaldehyde are introduced into a suspension of sodium acetate in acetanhydride acting at the same time as a solvent in this connection, and the mixture is heated to boiling for 3 – 8 h., preferably 6 h.

The compounds obtained according to the invention exhibit outstanding analgesic and neuroleptic properties, the presence of both properties together in one substance representing a surprising and novel fact. Those compounds of the general formula I wherein $R_1$ and $R_2$ are either directly or by a nitrogen atom connected to form a ring have proved to be especially effective in this connection. In addition, a marked spasmolytic activity — mostly combined with analgesic and/or sedative components — is found in numerous representatives of the products according to the invention.

The new substances can be processed into any type of preparation in use for pharmaceutical purposes; thus e.g. coated tablets, tablets, emulsions, solutions for injection etc. can be prepared from them.

EXAMPLE 1

1-Phenyl-4-dimethylamino-cyclohex-2-ene-1-carboxylic-acid-ethyl-ester . hydrochloride

Method A

1-Phenyl-2-acetoxy-cyclohex-3-ene-1-carboxylic-acid-ethyl-ester 1 mole (170 g) of ethyl atropate, 210 g of crotonaldehyde, 150 g of anhydrous sodium acetate and 0.6 l of acetanhydride are heated to boiling for 6 h. while stirring. Subsequently the main amount of the liquid phase is distilled off under vacuum, and the residue is extracted with 1 liter of hot ligroin. The residue of the ligroin phase is distilled. The product — although being pure according to gas chromatography — distills in a wide boiling range: b.p.$_{0,1}$ 130°–165°C. Yield: 105 g. It crystallizes when allowed to stand. M.P. 72°–73°C (from petroleum ether).

$C_{17}H_{20}O_4$ (288.4)

Calc.: C, 70.79; H, 6.99; O, 22.19. Found: C, 70.95; H, 7.15; O, 21.79.

1-Phenyl-2-hydroxy-cyclohex-3-ene-1-carboxylic-acid-ethyl-ester 75 g of the above product are heated under reflux for 10 hrs. in a mixture of 200 cc. of ethanol and 150 cc. of 2N NaOH. Most of the ethanol is removed in vacuum, the residue poured into water, and the aqueous phase extracted with ethyl acetate. Following drying, the solvent is removed, and the residue distilled. b.p.$_{0,1}$ 118°–120°C. Yield: 60 g.

$C_{15}H_{18}O_3$ (246.3)

Calc.: C, 73.14; H, 7.37; O, 19.48. Found: C, 72.56; H, 7.43; O, 20.10.

1-Phenyl-2-chloro-cyclohex-3-ene-1-carboxylic-acid-ethyl-ester

A solution of 60 g of the above cyclohexenol in 120 cc. of benzene is added drop by drop at a temperature below 50°C to a solution of 60 g of $PCl_5$ in 300 cc. of benzene. After stirring for 2 days at 20°C and subsequent washing with a large amount of water and a small amount of dilute sodium hydroxide solution, the benzene phase is dried over $CaCl_2$. The residue of the benzene phase is distilled. b.p.$_{0,01}$ 119°–121°C. Yield: 41 g.

$C_{15}H_{17}ClO_2$ (264.8)

Calc.: C, 68.04; H, 6.47; Cl, 13.40. Found: C, 67.54; H, 6.32; Cl, 13.00.

26 g (0.1 mole) of the above chlorocyclohexene are introduced into 150 cc. of a 10 % solution of dimethylamine in dimethylformamide. The product is allowed to stand over night, and the following day, during 7 hrs., a moderate stream of dimethylamine is conducted through the solution heated to 90°C. Then reduction in vacuum is effected, the residue taken up in 2 N HCl and freed of neutral substances with benzene. The aqueous phase is alkalized, and the separated oil taken up in ether. The hydrochloride is precipitated from the dried ethereal phase by means of a 10% solution of HCl gas in ethyl acetate. Yield: 30 g (crude), 16 g (p.a.). m.p. 158°–9°C (with 0,25.$H_2O$: 138°–9°C) (from dioxane-ether or ethyl acetate-isopropanol). $C_{17}H_{24}ClNO_2$ . 0,25 $H_2O$ (314.4)

Calc.: C, 64.94; H, 7.85; N, 4.46; Cl, 11.27. Found: C, 64.94; H, 7.59; N, 4.56; Cl, 10.91.

Method B

1-Phenyl-2-chloro-cyclohex-3-ene-carboxylic-acid-ethyl-ester 200 g of 1-phenyl-2-acetoxy-cyclohex-3-ene-1-carboxylic-acid-ethyl-ester are dissolved in 1 liter of 96% ethanol. The solution is charged with 190 g of HCl gas and heated under reflux for 2 hrs. The solvent is removed and the residue directly fractionated in the vacuum, b.p.$_{0,1}$ 130°C. Yield: 169 g. Gaschromatographically homogeneous. Infrared spectroscopically identical with the product prepared according to A.

20 g of this compound are reacted with dimethylamine in dimethylformamide according to Method A. 8 g of the hydrochloride of the above compound are obtained as the 0,25-hydrate with an melting point of 137°–9°C by process as described under A.

Method C

While shaking, 2.5 g of freshly distilled methane sulfonic acid chloride are added drop by drop at 5°C to 5 g of 1-phenyl-2-hydroxy-cyclohex-3-ene-1-carboxylic-acid-ethyl-ester dissolved in 10 ml of pyridine. The batch is allowed to stand for 3 days at 5°C, then it is poured into 100 ml of 2N HCl and extracted with benzene. The benzene residue forms a non-distillable oil, which is thin-layer-chromatographically homogeneous and which proves infrared spectroscopically to be the mesylate of the cyclohexanol. 2 g of the mesylate are taken up with 10 cc. of a 10% dimethylamine solution in dimethylformamide, and kept for 24 hrs. at 20°C and for 2 hrs. at 90°C. The product is introduced into diluted HCl and, after removing the neutral substances, alkalized with 2N NaOH. The hydrochloride of the above compound is precipitated as described, after taking up the separated base in ethyl acetate. Yield 0.5 g of the melting point 158°–9°C (anhydrous).

$C_{17}H_{24}ClNO_2$ (309.89)

Calc.: Cl, 11.45., Found: Cl, 11.46

Method D

1-Phenyl-2-iodo-cyclohex-3-ene-1-carboxylic-acid-ethyl-ester 27.3 g (0.1 mole) of 1-phenyl-2-dimethylamine-cyclohex-3-ene-1-carboxylic-acid-ethyl-ester are heated with 28.4 g (0.2 moles) of methyl iodide for 5 hrs. to 60°C in 100 cc. of dioxane. After cooling, it is sucked off from the tetramethylammonium iodide (19.9 g). The dioxane phase is evaporated at 40°C in vacuum, the residue taken up in benzene and extracted with 1N HCl. The benzene phase is washed with water and under protection from light is distilled off in vacuum. Residue: 35 g of dark-red, non-distillable oil.

$C_{15}H_{17}JO_2$ (356.2)

Calc.: J, 35.5. Found: J, 30.0.

35 g of the iodo-cyclohexene are taken up in 100 cc. of benzene, treated with a solution of 13.8 g of dimethylamine in 200 cc. of benzene and preserved in a dark place at room temperature for 24 hrs. 19.4 g of dimethylamine . hydro-iodide are filtered off. Then the benzene phase is extracted with 2N HCl, and the aqueous phase alkalized. 6.0 g of hydrochloride of the melting point 160°C (anhydrous) are precipitated as described under A from the dried ethereal extract.

$C_{17}H_{24}ClNO_2$ (309.89)

Calc.: Cl, 11.45. Found: Cl, 11.21.

Methoiodide 2.7 g of 1-phenyl-4-dimethylamino-cyclohex-2-ene-1-carboxylic-acid-ethyl-ester are dissolved in 10 cc. of dioxane and 1.5 g of $CH_3J$. The solution warms and the metho-iodide precipitates. Yield: 4 g, m.p. 191°–2°C (from methanol).

$C_{18}H_{26}JNO_2$ (415.32)

Calc.: J, 30.56. Found: J, 30.67.

EXAMPLE 2

1-Phenyl-4-diethylamino-cyclohex-2-ene-1-carboxylic-acid-ethyl-ester . hydrochloride 40 g of 1-phenyl-2-chloro-cyclohex-3-ene-1-carboxylic-acid-ethyl-ester are heated for 3 hrs. to 90°C in a covered glass autoclave with a solution of 45 g of diethylamine in 200 cc. of dimethylformamide. The solvent is distilled off in vacuum, and the residue, processed as described in example 1, method A. The hydrochloride is precipitated from ethyl acetate. Yield: 10.0 g, m.p. 135°–7°C (from methyl ethyl ketone).

$C_{19}H_{28}ClNO_2$ (337.9)

Calc.: C, 67.53; H, 8.35; Cl, 10.49; N, 4.14. Found: C, 67.48; H, 8.14; Cl, 10.21; N, 4.31.

EXAMPLE 3

1-Phenyl-4-N-morpholino-cyclohex-2-ene-1-carboxylic-acid-ethyl-ester . hydrochloride

Method A 44 g of 1-phenyl-2-chloro-cyclohex-3-ene-1-carboxylic-acid-ethyl-ester are dissolved in 250 cc. of dimethylformamide and incubated for 3 hrs. at 90°C with 45 g of morpholine. The product is then poured into 2N HCl, freed of neutral substances by extracting with toluene and then again set free by alkalizing with 2N NaOH. It is taken up in ether and precipitated as hydrochloride by means of HCl gas. The hydrochloride is digested with diisopropyl ether and then recrystallized from ethyl methyl ketone. Yield: 9.5 g, m.p. 173°–6°C.

$C_{19}H_{26}ClNO_3$ (351.86)

Calc.: C, 64.85; H, 7.45; Cl, 10.08; N, 3.98. Found: C, 64.80; H, 7.42; Cl, 9.84; N, 3.92.

Method B

1-Phenyl-2-bromo-cyclohex-3-ene-1-carboxylic-acid-ethyl-ester 14.2 g of 1-phenyl-2-hydroxy-cyclohex-3-ene-1-carboxylic-acid-ethyl-ester are heated to boiling for 30 minutes with 40 cc. of acetyl bromide. Then the product is taken up in toluene and washed until free of acid. The residue of the dried toluene phase is distilled in vacuo. b.p.$_{0,5}$ 142°C. Yield: 16,4 g, $n_D^{20}$ 1.5592.

6.2 of this compound are heated for 2 hrs. to 100°C with 6.0 g of morpholine in 25 cc. of DMSO. After cooling the product is introduced into water, and the separated base taken up in ether. Following extraction with water, the organic phase is dried, and the hydrochloride of the above compound precipitated by introducing HCl gas. Yield: 5.0 g, m.p. 176°C.

$C_{19}H_{26}ClNO_3$ (351.86)

Calc.: C, 64.85; H, 7.45; Cl, 10.08; N, 3.98. Found: C, 64.76; H, 7.45; Cl, 10.26; N, 3.97.

EXAMPLE 4

1-Phenyl-4-(2-phenylethylamino)-cyclohex-2-ene-1-carboxylic-acid-ethyl-ester . hydrochloride

Method A 40 g of 1-phenyl-2-chloro-cyclohex-3-ene-1-carboxylic-acid-ethyl-ester and 36 g of β-phenylethylamine in 250 cc. of dimethylformamide are heated for 3 hrs. to 90°C. The solvent is removed under vacuum in the rotary evaporator, and the residue introduced into water. Extraction is effected with toluene, and the toluene phase saturated with aqueous 2N HCl. On standing, the hydrochloride, which is sparingly soluble in water, separates. Recrystallization from benzene is effected. Yield: 16.9 g, m.p. 179°–82°C.

$C_{23}H_{28}ClNO_2$ (385.92)

Calc.: C, 71.58; H, 7.31; N, 3.63; Cl, 9.19. Found: C, 71.66; H, 7.11; N, 3.87; Cl, 9.87.

Method B 15 g of 1-phenyl-2-hydroxy-cyclohex-3-ene-1-carboxylic-acid-ethyl-ester and 15 cc. of thionyl chloride and 1 cc. of dimethylformamide are heated under reflux for 10 minutes. Then direct distillation is done. 12.2 g of 1-phenyl-2-chloro-cyclohex-3-ene-1-carboxylic-acid-ethyl-ester of the boiling point 0.1/122°–5°C are obtained. By reacting with 12 g of β-phenylethyl amine in 100 cc. of DMSO for 2 hrs. at 100°C, processing as described above, 6.0 g of hydrochloride m.p. 179°–82°C are obtained.

EXAMPLE 5

1-Phenyl-4-(N$_4$-phenyl-N$_1$-piperazino(-cyclohex-2-ene-1-carboxylic-acid-ethyl-ester . hydrochloride

Method A 50 g of N-phenyl-piperazine and 35 g of 1-phenyl-2-chloro-cyclohex-3-ene-1-carboxylic-acid-ethyl-ester are dissolved in 250 cc. of dimethylformamide and heated for 3 hrs. to 90°C. The solvent is distilled off, and the residue digested with 1.5 l of water. The pH-value is adjusted to 5 by means of diluted HCl, the undissolved material filtered off and taken up in chloroform. This phase is washed with water, dried and concentrated. The residue is taken up in benzene and precipitated as hydrochloride by introducing HCL gas. Yield: 12.2 g (from benzene), m.p. 193°–5°C.

$C_{25}H_{31}ClN_2O_2$ (426.97)

Calc.: C, 70.33; H, 7.32; Cl, 8.30; N, 6.56. Found: C, 70.37; H, 7.35; Cl, 8.13; N, 6.37.

Method B

Following addition of 5 g of N-phenyl-piperazine, a solution of 4.0 g of 1-phenyl-2-bromo-cyclohex-3-ene-1-carboxylic-acid-ethyl-ester in 20 cc. of DMSO is kept at 100°C for 2 hrs. After adding 100 cc. of toluene, extraction with water is effected several times and then the toluene phase dried over $CaCl_2$. The residue from this phase is taken up in ether and precipitated by dropwise adding ethereal hydrochloric acid. Yield following recrystallization from benzene: 4.0 g, m.p. 198°–200°C.

$C_{25}H_{31}ClN_2O_2$ (426.97)

Calc.: C, 70.33; H, 7.32; Cl, 8.30; N, 6.56. Found: C, 70.32; H, 7.37; Cl, 8.48; N, 6.27.

Method C 35 g of 1-phenyl-2-iodo-cyclohex-3-ene-1-carboxylic-acid-ethyl-ester are dissolved in 200 cc. of dioxane, and 32 g of phenyl-piperazine are added to the solution. After 2 hrs., filtration from the phenyl-piperazine-hydro-iodide (30 g) is effected, and the crude base (33.8 g) is obtained by distilling off the dioxane. After this mild preparation, the base is so pure that it crystallizes: m.p. 95°–96°C (from hexane). 21.6 g of hydrochloride with m.p. 200°C may be prepared from it.

EXAMPLE 6

1-Phenyl-4-benzylamino-cyclohex-2-ene-1-carboxylic-acid-ethyl-ester . oxalate 40 g of 1-phenyl-2-chloro-cyclohex-3-ene-1-carboxylic-acid-ethyl-ester are dissolved in 400 cc. of dry acetonitrile and, following addition of 48 g of benzylamine, heated to boiling for 2 hrs. The solvent is distilled off, and the residue taken up in 2N HCl. The neutral products are extracted with ether. The aqueous phase is alkalized and the separated oil precipitated from ethyl acetate with oxalic acid. Yield: 11.8 g, m.p. 207°C (from methanol).

$C_{24}H_{27}O_6N$ (425.46)

Calc.: C, 67.74; H, 6.40; N, 3.30. Found: C, 67.38; H, 6.37; N, 3.66.

EXAMPLE 7

1-Phenyl-4-methylamino-cyclohex-2-ene-1-carboxylic-acid-ethyl-ester . hydrochloride 40 g of 1-phenyl-2-chloro-cyclohex-3-ene-1-carboxylic-acid-ethyl-ester are dissolved in 250 cc. of monomethylformamide and saturated with methylamine at 2 atmospheres. The product is warmed for 4 hrs. to 70°C in a glass autoclave, then poured into 1.5 l of water and acidified with 2N HCl. The ether extract is discarded and the aqueous phase precipitated as hydrochloride with HCl-gas in ether. Yield: 19.2 g (from isopropanol), m.p. 162°–3°C.

$C_{16}H_{22}ClNO_2$ (395.8)

Calc.: C, 64.96; H, 7.50; Cl, 11.99; N, 4.73. Found: C, 65.04; H, 7.49; Cl, 11.71; N, 5.04.

Example 8

1-Phenyl-4-amino-cyclohex-2-ene-1-carboxylic-acid-ethyl-ester . naphthalene-1,5-disulfonate 45 g of 1-phenyl-2-hydroxy-cyclohex-3-ene-1-carboxylic-acid-ethyl-ester are introduced into 320 cc. of absolute ethanol charged with 8% gaseous HCl. The product is allowed to stand for 24 hrs. at 20°C, then the solvent and the excess HCl are removed in vacuo, and the residue taken up in 400 cc. of fresh ethanol. Following addition of 1 g of $NH_4Cl$, $NH_3$ is pressed on for 5 hrs. at 80°C under 5 atmospheres. It is distilled to dryness, and the residue taken up in 2N HCl. It is freed of the neutral part in the usual manner and alkalized. The base is taken up in ether; removal of the solvent is effected, and the residue precipitated in isopropanol as naphthalene-1,5-disulfonate. Yield: 11 g, m.p. 325°C (from ethanol).

$C_{40}H_{46}N_2O_{10}S_2$ (778.92)

Calc.: C, 61.68; H, 5.95; N, 3.58; S, 8.23. Found: C, 61.60; H, 6.11; N, 3.80; S, 8.18.

EXAMPLE 9

1-Phenyl-4-(N-metnyl-N-allyl-amino)-cyclohex-2-ene-1-carboxylic-acid-ethyl-ester . hydrochloride 30 g of 1-phenyl-2-chloro-cyclohex-3-ene-1-carboxylic-acid-ethyl-ester together with 19.5 g of N-methyl-N-allylamine are heated for 1 hr. to 90°C in a mixture of 300 cc. of dimethylformamide and 60 cc. of toluene. Processing is effected as described in example 7. Yield: 8.8 g of hydrochloride, m.p. 153°–5°C (from isopropanol-ethyl acetate).

$C_{19}H_{26}ClNO_2$ (335.88)

Calc.: C, 67.73; H, 7.65; Cl, 10.59; N, 3.83. Found: C, 67.93; H, 7.80; Cl, 10.56; N, 3.17.

EXAMPLE 10

1-Phenyl-4-($N_4$-methyl-piperazino)-cyclohex-2-ene-1-carboxylic-acid-ethyl-ester . dihydrochloride 26.5 g of 1-phenyl-2-chloro-cyclohex-3-ene-1-carboxylic-acid-ethyl-ester, 11 g of N-methyl-piperazine and 22 g of ethyl-diisopropylamine are heated for 10 minutes on the oil bath to 126°C. After cooling, the product is taken up in ether, sucked off, the ether phase is dried, and the residue taken up in chloroform. Extraction is effected with water, the dried $CHCl_3$ phase concentrated. The residue is taken up in ether and the hydrochloride is precipitated with HCl gas. Yield: 12.0 g, m.p. 233°–5°C (from isopropanol).

$C_{20}H_{30}Cl_2N_2O_2$ (401.36)

Calc.: C, 59.85; H, 7.53; Cl, 17.66; N, 6.98. Found: C, 59.59; H, 7.41; Cl, 17.30; N, 6.81.

EXAMPLE 11

1-Phenyl-4-($N_4$-2-phenylethyl-piperazino)-cyclohex-2-ene-1-carboxylic-acid-ethyl-ester . dihydrochloride 26.5 g of 1-phenyl-2-chloro-cyclohex-3-ene-1-carboxylic-acid-ethyl-ester are heated for 2 hrs. to 150°C with 0.1 mole of β-phenylethyl-piperazine and 22 g of ethyl-diisopropylamine. After cooling, the product is taken up in ether; the ether phase is filtered and evaporated. The residue is taken up in fresh ether and saturated with 1N HCl. The dihydrochloride, which is sparingly soluble in water and ether, separates. It is recrystallized from isopropanol. Yield: 13.0 g, m.p. 272°–3°C.

$C_{27}H_{36}Cl_2N_2O_2$ (491.51)

Calc.: C, 65.97; H, 7.39; Cl, 14.42; N, 5.70. Found: C, 65.94; H, 7.50; Cl, 14.27; N, 5.69.

EXAMPLE 12

1-Phenyl-4-($N_4$-benzyl-piperazino)-cyclohex-2-ene-1-carboxylic-acid-ethyl-ester . dihydrochloride 26.5 g of 1-phenyl-2-chloro-cyclohex-3-ene-1-carboxylic-acid-ethyl-ester, 17.7 g of N-benzyl-piperazine and 22 g of ethyl-diisopropylamine are heated first for 30 minutes to 100°C and then for 15 minutes to 150°C. Processing is effected as described in example 11; after recrystallization from isopropanol, 15.2 g, m.p. 251°–3°C are obtained.

$C_{26}H_{34}Cl_2N_2O_2$ (477.46)

Calc.: C, 65.40; H, 7.18; Cl, 14.86; N, 5.87. Found: C, 65.20; H, 6.97; Cl, 14.44; N, 5.61.

EXAMPLE 13

1-Phenyl-4-($N_4$-4'-methoxyphenyl-piperazino)-cyclohex-2-ene-1-carboxylic-acid-ethyl-ester . hydrochloride 20 g of 1-(p-methoxy-phenyl)-piperazine are dissolved in 200 cc. of DMSO, mixed with 25 g of 1-phenyl-2-chloro-cyclohex-3-ene-1-carboxylic-acid-ethylester and 20 g of N-ethyl-diisopropylamine and heated for 3 hrs. to 100°C. After distilling off the solvent, the residue is digested with 0.5N HCl and after decanting taken up in ether. On standing, the hydrochloride separates. It is recrystallized from benzene. Yield: 3.0 g, m.p. 190°–1°C.

$C_{26}H_{33}ClN_2O_3$ (457.03)

Calc.: C, 68.33; H, 7.28; Cl, 7.76; N, 613. Found: C, 68.17; H, 7.07; Cl, 7.93; N, 6.07.

EXAMPLE 14

1-Phenyl-4-($N_4$-2'-methoxyphenyl-piperazino)-cyclohex-2-ene-1-carboxylic-acid-ethyl-ester . hydrochloride Preparation as described in example 13. Yield: 8.3 g, m.p. 182°–3°C (from benzene).

$C_{26}H_{33}ClN_2O_3$ (457.03)

Calc.: C, 68.33; H, 7.28; Cl, 7.76; N, 6.13. Found: C, 68.21; H, 7.40; Cl, 7.80; N, 6.28.

EXAMPLE 15

1-Phenyl-4-($N_4$-4'-chlorophenyl-piperazino)-cyclohex-2-ene-1-carboxylix-acid-ethyl-ester . hydrochloride Preparation as described in example 13 (20 g of $N_1$-(4-chloro-phenyl)-piperazine). Yield: 14.0 g, m.p. 198°–200°C (from benzene or isopropanol).

$C_{25}H_{30}Cl_2N_2O_2$ (461.45)

Calc.: C, 65.07; H, 6.56; Cl, 15.37; N, 6.07. Found: C, 65.14; H, 6.73; Cl, 15.22; N, 5.75.

EXAMPLE 16

1-Phenyl-4-(4'-benzyl-piperidino)-cyclohex-2-ene-1-carboxylic-acid-ethyl-ester . hydrochloride 30 g of 1-phenyl-2-chloro-cyclohex-3-ene-1-carboxylic-acid-ethyl-ester are heated together with 45 g of benzylpiperidine in 150 cc. of DMSO for 2½ hrs. to 100°C. The product is poured into 1.5 l of ice water, acidified with 1N HCl and extracted with ether. An oil, which crystallizes on digestion with water, separates from the ether phase. Recrystallization is effected first from toluene, then from ethyl acetate. Yield: 19.0 g, m.p. 142°C (as semihydrate).

$C_{27}H_{35}ClNO_{2.5}$ (449.05)

Calc.: C, 72.21; H, 7.86; Cl, 7.90; N, 3.12. Found: C, 72.16; H, 7.83; Cl, 7.80; N, 3.01.

EXAMPLE 17

1-Phenyl-4-N-piperidino-cyclohex-2-ene-1-carboxylic-acid-ethyl-ester . hydrochloride Method A 57.6 g of 1-phenyl-2-acetoxy-cyclohex-3-ene-1-carboxylic-acid-ethyl-ester and 160 cc. of thionyl-chloride and 3.6 cc. of water are heated under reflux for 30 minutes. The whole is distilled off in the rotary evaporator to 100°C/20 Torr, the residue is taken up in 100 cc. of DMSO, and 30 g of piperidine are added. The batch is heated for 3 hrs. to 100°C, then poured into ice water and adjusted to pH 3 by means of 2N HCl. Neutral products are removed with toluene. The aqueous phase is alkalized with ammonia and the separated oil taken up in ether. The hydrochloride is precipitated from the dried ether phase by means of HCl gas. Yield: 20.2 g, m.p. 216°–7°C (from isopropanol).

$C_{20}H_{28}ClNO_2$ (349.91)

Calc.: C, 68.65; H, 8.06; Cl, 10.13; N, 4.00. Found: C, 68.95; H, 8.19; Cl, 10.09; N, 4.30.

Method B 35 g of 1-phenyl-2-iodo-cyclohex-3-ene-1-carboxylic-acid-ethyl-ester are taken up in 200 cc. of dioxane, 17 g of piperidine are added and preserved for 12 hrs. at room temperature in a dark place. Then most of the solvent is distilled off, and the residue introduced into 300 cc. of water. Extraction is effected with ether, and the hydrochloride precipitated from the washed and dried phase by means of HCl gas. Yield: 29.0 g, m.p. 215°–17°C (from isopropanol).

EXAMPLE 18

1-Phenyl-4-($N_4$-3'-chlorophenyl-piperazino)-cyclohex-2-ene-1-carboxylic-acid-ethyl-ester. hydrochloride Preparation is effected as described in example 15. Yield: 10.5 g, m.p. 188°–90°C (from isopropanol).

$C_{25}H_{30}Cl_2N_2O_2$ (461.45)

Calc.: C, 65.07; H, 6.56; Cl, 15.37; N, 6.07. Found: C, 64.88; H, 6.49; Cl, 15.28; N, 5.85.

EXAMPLE 19

1-Phenyl-4-(4'-phenyl-piperidino)-cyclohex-2-ene-1-carboxylic-acid-ethyl-ester . hydrochloride 32 g of 1-phenyl-2-chloro-cyclohex-3-ene-1-carboxylic-acid-ethyl-ester are dissolved in 100 cc. of dioxane, 16 g of 4-phenyl-piperidine and 30 g of ethyl-diisopropylamine are added and heated for 3 hrs. to 100°C. Processing is effected as described in example 13. Yield: 12 g, m.p. 238°–40°C (from toluene).

$C_{26}H_{32}ClNO_2$ (426.01)

Calc.: C, 73.30; H, 7.57; Cl, 8.32; N, 3.29. Found: C, 73.09; H, 7.65; Cl, 8.35; N, 3.46.

EXAMPLE 20

1-Phenyl-4-($N_4$-benzoyl-piperazino)-cyclohex-2-ene-1-carboxylic-acid-ethyl-ester . hydrochloride 35 g of N-benzoyl-piperazine and 40 g of 1-phenyl-2-chloro-cyclohex-3-ene-1-carboxylic-acid-ethyl-ester and 35 g of ethyl-diiosopropylamine in 100 cc. of DMSO are heated for 2½ hrs. to 100°C. Processing is effected as described in example 13. Yield: 12.5 g, m.p. 185°–7°C (from isopropanol).

$C_{26}H_{34}ClN_2O_3$

Calc.: C, 68.63; H, 6.87; Cl, 7.79; N, 6.16. Found: 68.69; H, 7.02; Cl, 7.84; N, 6.14.

EXAMPLE 21

1-Phenyl-4-(4'-methyl-piperidino)-cyclohex-2-ene-1-carboxylic-acid-ethyl-ester . hydrochloride 25 g of 1-phenyl-2-chloro-cyclohex-3-ene-1-carboxylic-acid-ethyl-ester, 30 g of 4-methyl-piperidine and 100 cc. of DMSO are heated for 3 hrs. to 100°C. Most of the solvent is distilled off in vacuo, and the residue acidified with 2N HCl, the hydrochloride is separating. It is recrystallized from isopropanol. Yield: 23.3 g, m.p. 220°–22°C.

$C_{21}H_{30}ClNO_2$ (363.94)

Calc.: C, 69.30; H, 8.31; Cl, 9.74; N, 3.85. Found: C, 69.15; H, 8.38; Cl, 9.66; N, 3.73.

EXAMPLE 22

1-Phenyl-4-(4'-hydroxy-piperidino)-cyclohex-2-ene-1-carboxylic-acid-ethyl-ester . oxalate 20 g of 1-phenyl-2-chloro-cyclohex-3-ene-1-carboxylic-acid-ethyl-ester are heated for 3 hrs. to 100°C with 20 g of 4-hydroxypiperidine and 100 cc. of DMSO. Then the product is diluted with toluene and extracted with water and then with 2N HCl, and the hydrochloric phase alkalized with 2N NaOH. The separated phase is taken up in ethyl acetate and precipitated with oxalic acid. Yield: 5.3 g (from acetonitrile-ethyl acetate), m.p. 166°–8°C.

$C_{42}H_{56}N_2O_{10}$ (748.92)

Calc.: C, 67.36; H, 7.54; N, 3.75. Found: C, 67.08; H, 7.38; N, 3.54.

EXAMPLE 23

1-Phenyl-4-(N-methyl-N-β-phenethyl-amino)-cyclohex-2-ene-1-carboxylic-acid-ethyl-ester . hydrochloride 22 g of 1-phenyl-2-chloro-cyclohex-3-ene-1-carboxylic-acid-ethyl-ester are dissolved in 100 cc. of DMSO and heated for 3 hrs. to 110°C together with 22 g of N-methyl-N-β-phenethylamine. The product is acidified with diluted HCl and extracted with toluene. On cooling to 5°C, the hydrochloride separates. It is digested with cold $CHCl_3$ and recrystallized from toluene. Yield: 14.2 g, m.p. 148°–150°C.

$C_{24}H_{30}ClNO_2$ (399.97)

Calc.: C, 72.07; H, 7.56; Cl, 8.86; N, 3.50. Found: C, 72.21; H, 7.61; Cl, 8.92; N, 3.42.

EXAMPLE 24

1-Phenyl-4-(di-n-butylamino)-cyclohex-2-ene-1-carboxylic-acid-ethyl-ester . hydrochloride 35 g of 1-phenyl-2-iodo-cyclohex-3-ene-1-carboxylic-acid-ethyl-ester are dissolved in 250 cc. of dioxane, mixed with 26 g of di-n-butylamine and preserved for 20 hrs. at room temperature in a dark place. Then the product is introduced into sufficient 2N HCl, extracted with ether, and the aqueous phase alkalized with ammonia. The separated oil is taken up in ethyl acetate and washed with water several times. By the addition of a solution of HCl gas in ethyl acetate, the hydrochloride is separated; it is recrystallized from isopropanol by adding ethyl acetate. Yield: 11.3 g, m.p. 123°–4°C $C_{23}H_{35}ClNO_2$ (392.97)

Calc.: C, 70.29; H, 8.98; Cl, 9.02; N, 3.56. Found: C, 70.11; H, 8.99; Cl, 9.20; N, 3.47.

According to the same method, there can also be prepared

25.

1-[N-methyl-N-(α-methyl-β-hydroxyphenethyl)-amino]-4-phenyl-4-ethoxycarbonyl-cyclohexene-(2) · HCl $C_{25}H_{32}ClNO_4$ (430.0) M.p. 231°–4° (from ethanol)

Calc. Cl, 8.25. Found Cl, 8.27.

$R_1 = CH_3$

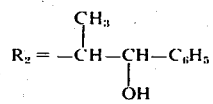

26.

1-N-piperidino-4-phenyl-4-ethoxycarbonyl-cyclohexene-(2) · methiodide $C_{21}H_{30}INO_2$ (455.4)

Calc. I, 27.87. Found I, 27.66.

M.p. 185°–6° (from isopropanol)

27.

1-N-methyl-N-γ-phenylpropylamino-4-phenyl-4-ethoxycarbonyl-cyclohexene-(2) · HCl $C_{25}H_{32}ClNO_2$ (414.0)

Calc. Cl, 8.56. Found Cl, 8.87.

M.p. 149°–52° (from toluene)

$R_1 = CH_3$ $R_2 = C_6H_5(CH_2)_3-$ and

28.

1-N-methyl-N-β-phenylisopropylamino-4-phenyl-4-ethoxycarbonyl-cyclohexene-(2)·HCl $C_{25}H_{32}ClNO_2$ (414.0)

Calc. Cl, 8.56. Found Cl, 8.56.

M.p. 148°–1° (from toluene).

We claim:

1. 1-Phenyl-4-dimethylamino-cyclohex-2-ene-1-carboxylic-acid-ethylester.
2. 1-Phenyl-4-diethylamino-cyclohex-2-ene-1-carboxylic-acid-ethylester.
3. 1-Phenyl-4-(2-phenylethylamino)-cyclohex-2-ene-1-carboxylic-acid-ethyl-ester.
4. 1-Phenyl-4-benzylamino-cyclohex-2-ene-1-carboxylic-acid-ethyl-ester.
5. 1-Phenyl-4-methylamino-cyclohex-2-ene-1-carboxylic-acid-ethylester.
6. 1-Phenyl-4-amino-cyclohex-2-ene-1-carboxylic-acid-ethyl-ester.
7. 1-Phenyl-4(methylallyl-amino)-cyclohex-2-ene-1-carboxylic-acid-ethylester.
8. 1-Phenyl-4-(methyl-2-phenylethyl-amino)-cyclohex-2-ene-1-carboxylic-acid-ethylester.
9. 1-Phenyl-4-(di-n-butylamino)-cyclohex-2-ene-1-carboxylic-acid-ethylester.

* * * * *